United States Patent [19]

Rossey et al.

[11] Patent Number: 5,081,277
[45] Date of Patent: Jan. 14, 1992

[54] PROCESS FOR THE PREPARATION OF PROPIONIC ACID DERIVATIVES

[75] Inventors: Guy Rossey, Voisins le Bretonneux; Antonio Ugolini, Le Pecq; Isaac Chekroun, Epinay; Abkar Vartanian, Meulan; Alexander Wick, Saint Nom la Breteche, all of France

[73] Assignee: Synthelabo, Paris, France

[21] Appl. No.: 416,499

[22] Filed: Oct. 3, 1989

[30] Foreign Application Priority Data

Oct. 3, 1988 [FR] France .................. 88 12888

[51] Int. Cl.⁵ .............................................. C07B 57/00
[52] U.S. Cl. ..................................... 560/17; 562/401; 562/431
[58] Field of Search .................... 562/401, 431; 560/17

[56] References Cited

U.S. PATENT DOCUMENTS

| | | | |
|---|---|---|---|
| 4,420,628 | 12/1983 | Inoue et al. | 560/17 |
| 4,567,175 | 1/1986 | Takeda et al. | 514/211 |
| 4,585,768 | 4/1986 | Takeda et al. | 514/211 |
| 4,665,068 | 5/1987 | Takeda et al. | 514/211 |

FOREIGN PATENT DOCUMENTS 61-145159 2/1986 Japan.
61-145160 2/1986 Japan.
61-145174 2/1986 Japan.

*Primary Examiner*—Jose G. Dees
*Assistant Examiner*—Vera C. Clarke
*Attorney, Agent, or Firm*—Fleit, Jacobson, Cohn, Price, Holman & Stern

[57] ABSTRACT

Process for the preparation of compounds of the general formula (I)

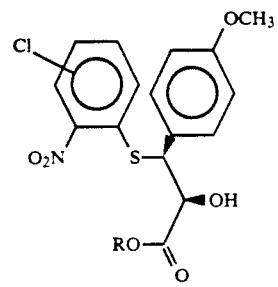

wherein R is hydrogen or $(C_{1-4})$alkyl.

6 Claims, No Drawings

PROCESS FOR THE PREPARATION OF PROPIONIC ACID DERIVATIVES

The present invention is directed to a process for the preparation of propionic acid derivatives.

According to said process, it is possible to prepare directly the optically pure (2S, 3S) diastereoisomers of compounds of the general formula (I)

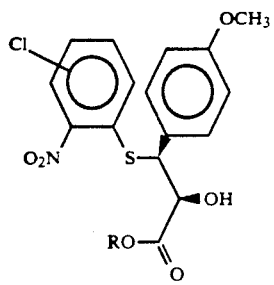

wherein R is hydrogen or ($C_{1-4}$) alkyl.

The process comprises reacting a thiophenol of general formula (II)

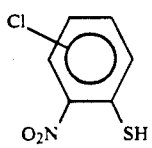

with a compound of general formula (III)

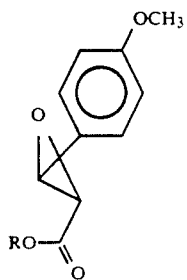

and, if desired, hydrolyzing the alkyl ester so as to obtain the corresponding acid.

The reaction between a compound (II) and a compound (III), who are disclosed in the literature, can be carried out by heating, under inert atmosphere, in an inert solvent such as tetrahydrofuran, dioxan, nitromethane, dimethylformamide, a dichloroalcane, toluene or another aromatic solvent, for 1 to 10 hours, depending on the temperature.

The starting compound (III) (methyl ester), in the form of the (−) (2R,3S) isomer, is described in Japanese patent applications No. 145,159/1986, 145,160/1986 and 145,174/1986.

The compounds (I), prepared according to the invention, are useful for the preparation of benzothiazepinone derivatives, especially chlorinated derivatives of Diltiazem.

Some compounds of formula (I) are new and belong to the invention, especially the (2S,3S) 3-(6-chloro-2-nitrophenylthio)-2-hydroxy-3-(4-methoxyphenyl)-propionic acid.

The following examples illustrate the invention. The IR and NMR spectra structures of the compounds obtained.

EXAMPLE 1

Methyl (2S,3S) 3-(6-chloro-2-nitrophenylthio)-2-hydroxy-3-(4-methoxyphenyl)-propionate In a 25 ml flask equipped with thermometer and nitrogen admission, there are introduced 22 mg of zinc acetate dihydrate, 948 mg of 6-chloro-2-nitrothiophenol and 5 ml of toluene. To the suspension are added dropwise, within 5 mn, a solution of 1.093 g of methyl (−) (2R,3S) 3-(4-methoxyphenyl)-2,3-epoxy-propionate in 7.5 ml of toluene at 25° C. The temperature rises to 27°-28° C., whilst stirring is maintained for 1.5 hour. The mixture is evaporated in vacuo, and a yellow oil is obtained, which is used as it is in the subsequent example.

EXAMPLE 2

(+) (2S,3S) 3-(6-chloro-2-nitro-phenylthio)-2-hydroxy-3-(4-methoxyphenyl)-propionic acid In a 50 ml flask there are introduced 2 g of the ester prepared according to example 1, dissolved in 10 ml of methanol.

To this solutions are added 13 ml of water and 0.6 ml of 10N sodium hydroxide.

The mixture is stirred at 25°-28° C. for 3 hours, then cooled in an ice bath, and the pH is adjusted to 1 by addition of concentrated hydrochloric acid. The methanol is evaporated, and a sticky precipitate is obtained.

It is left in the refrigerator for 16 hours, filtered off, washed with water. The sticky insoluble product is triturated in ethyl acetate, a suspension is obtained, which is filtered, washed with ethyl acetate. The product is dried in vacuo, and the raw acid is recrystallized in 10 ml of ethyl acetate at reflux temperature. Yield: 62.6%.

M. P.:186°-188° C. (yellow crystals).
$[\alpha]_D^{20} = +76.3°$ (c=0.5, MeOH)
$[\alpha]_D^{20} = +27.6°$ (c=0.5, NaON 1N).

EXAMPLE 3

Methyl (2S,3S) 3-(5-chloro-2-nitro-phenylthio)-2-hydroxy-3-(4-methoxyphenyl)-propionate In a 25 ml flask equipped with thermometer and nitrogen admission, there are introduced 26 mg of zinc acetate dihydrate, 948 mg of 5-chloro-2-nitrothiophenol and 5 ml of toluene. To the suspension are added dropwise, within 5 mn, a solution of 1.093 g of methyl (−) (2R,3S) 3-(4-methoxyphenyl)-2,3-epoxy-propionate in 9 ml of toluene at 25° C. The temperature rises to 29° C., whilst stirring is maintained for 45 mn. The mixture is evaporated in vacuo, and a yellow oil is obtained, which is used as it is in the subsequent example.

EXAMPLE 4

(+) (2S,3S) 3-(5-chloro-2-nitro-phenylthio)-2-hydroxy3-(4-methoxyphenyl)-propionic acid In a 50 ml flask there are introduced 2 g of the ester prepared according to example 3, then 14 ml of methanol and 22 ml of water.

A product precipitates. 0.6 ml of 10N sodium hydroxide are added, and the stirring is maintained for 3 hours. The mixture is filtered, the filtrate is cooled in an ice bath, and acidified with 0.7 ml of concentrated hydrochloric acid until pH=1. The acid formed is filtered off, washed with water and dried in vacuo in the presence of phosphoric anhydride for 16 hours, and at 50° C for 4 hours. 1.78 (97.2%) of raw acid are obtained, which are recrystallized in 8 ml of isopropyl alcohol at reflux temperature. The compound crystallizes with 0.2 mole of isopropyl alcohol.

M. P.: 120°-127° C. (M. P.=92°-97° C. with 1 mole of isopropyl alcohol, as indicated in the literature).

$[\alpha]_D^{20} = +132.5°$ (c=0.5, CHCl$_3$).

The compounds (I) prepared according to the process of the invention are intermediates for the synthesis of chlorinated benzothiazepinone derivatives, especially chlorinated derivatives of Diltiazem, according to methods disclosed e.g. in U.S. Pat. Nos. 3,562,257 and 4,567,175.

We claim:

1. A method of for the preparation of an optically pure (2S,3S) diastereoisomer of formula (I):

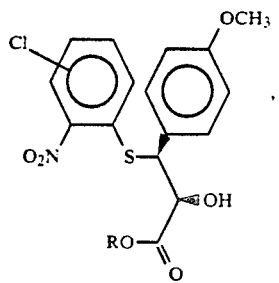

wherein R is hydrogen or (C$_{1-4}$) alkyl, comprising reacting a compound of formula (II):

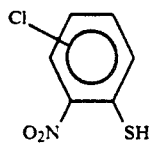

with a compound of formula (III):

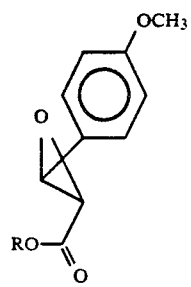

by heating under inert atmosphere, in an inert solvent, for 1 to 10 hours, wherein said reaction time is selected as a function of temperature and the compound of formula (III( is the (−) (2R, 3S) isomer.

2. A process according to claim 1, wherein R is methyl.

3. A process according to claim 1, wherein the solvent is toluene.

4. A process according to claim 1, wherein the temperature of the reaction between compounds (II) and (III) is between 20° and 30° C.

5. The method of claim 1, wherein sad inert solvent is selected from the group consisting of tetrahydrofuran, dioxan, nitromethane, dimethylformamide, a dichloroalkane, toluene and other inert aromatic solvents.

6. The method of claim 1, wherein the resulting product is an ester, further comprising hydrolyzing said ester to produce the corresponding acid.

* * * * *